United States Patent [19]

St. Georgiev et al.

[11] Patent Number: 4,727,157
[45] Date of Patent: Feb. 23, 1988

[54] 3-(SUBSTITUTED PHENYL)-3-(1H-1,2,4-TRIAZOL-1-YL)METHYL-2-METHYL-5-[(SUBSTITUTED PHENOXY)METHYL]ISOXAZOLIDINE DERIVATIVES

[75] Inventors: Vassil St. Georgiev, Rochester; George B. Mullen, Avon, both of N.Y.

[73] Assignee: Pennwalt Corporation, Philadelphia, Pa.

[21] Appl. No.: 900,857

[22] Filed: Aug. 27, 1986

[51] Int. Cl.$^4$ .......................................... C07D 249/08
[52] U.S. Cl. .................................. 548/240; 548/262; 568/630
[58] Field of Search ....................................... 548/240

[56] References Cited

U.S. PATENT DOCUMENTS

| 3,711,495 | 1/1973 | Kulsa et al. | 548/240 |
| 3,915,978 | 10/1975 | Kulsa et al. | 548/240 |
| 3,987,179 | 10/1976 | Nadelson | 514/378 |

FOREIGN PATENT DOCUMENTS 54-76579  6/1979  Japan .

OTHER PUBLICATIONS

Sokolov, S. V. et al., Chemical Abstract 55:7399 (1961) Abstracting "Isoxazale Compounds III, Synthesis of Some Isoxazolylazoles", Zhur. Obshchei Khim. 30, pp. 1781–1787 (1960).
Kano, H. et al., Chem. Abstract 62:9139a (1965), Abstracting French 1,376,432 (Oct. 23, 1964).
Kano, H. et al., Chemical Abstract 63:8367a (1965), Abstracting French 1,380,177 (Nov. 27, 1964).
Takahi, Y. et al., Chemical Abstract 81:22233c (1974), Abstracting Japan Kokai 7399,336 (Dec. 15, 1973).
Boyce, C. B. et al., Chemical Abstract 87:23258a (1977), Abstracting German offen. 2,639,189 (Mar. 10, 1977).
Funaki, Y. et al., Chemical Abstract 92:128915u (1980), Abstracting Japan Kokai 79 76,579 (Jun. 19, 1979).
Kelly, R. C. et al., Chemical Abstract 93:114498u (1980), Abstracting German Offen. 2,918,878 (Nov. 22, 1979).
Haken, P. T. et al., Chemical Abstract 93:132471; (1980), Abstracting Brit.Pat. Appln. 2,024,218 (Jan 9, 1980).

Primary Examiner—Donald G. Daus
Assistant Examiner—Barbara Cassatt

[57] ABSTRACT

3-(substituted phenyl)-3-(1H-1,2,4-triazol-1-yl)methyl-2-methyl-5-[(substituted phenoxy)methyl]isoxazolidine derivatives in which hydrogens of their phenyl rings may be replaced by halogen, lower alkyl, lower alkoxy, alkoxycarbonyl, alkanoylamino or nitro groups are useful as antifungal agents.

14 Claims, No Drawings

3-(SUBSTITUTED PHENYL)-3-(1H-1,2,4-TRIAZOL-1-YL)METHYL-2-METHYL-5-[(SUBSTITUTED PHENOXY)METHYL]ISOXAZOLIDINE DERIVATIVES

BACKGROUND OF THE INVENTION

This invention relates generally to substituted 2-methylisoxazolidine derivatives and more specifically to 3-(substituted phenyl)-3-(1H-1,2,4,-triazol-1-yl)methyl-2-methyl-5-[(substituted phenoxy)methyl]isoxazolidines which are useful as antifungal agents.

BRIEF SUMMARY OF THE INVENTION

In accordance with this invention there are provided compounds of the formula:

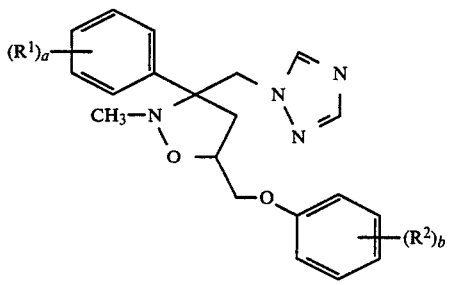

and pharmaceutically acceptable acid addition salts thereof, in the form of their enantiomers, or mixtures of their enantiomers including disastereoisomeric pairs of such enantiomers, wherein;
a=1 or 2,
b=1 or 2,
$R^1$ is selected from hydrogen, lower alkyl, halogen, lower alkoxy, and combinations thereof, provided the ortho position is hydrogen and $R^2$ is selected from hydrogen, lower alkyl, halogen, lower alkoxy, alkoxycarbonyl, alkanoylamino, nitro, and combinations thereof.

DETAILED DESCRIPTION OF THE INVENTION

The compounds of this invention are useful as antifungal agents. They have been shown to have in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 2-4, 6-9, and 12 were tested and found to have good to moderate inhibitory activity (minimum inhibitory concentrations, MIC, of 0.7 to 70 ug/ml) against epidermophyton floccosum. The compound of Example 11 had good (0.7 to 2 ug/ml) activity against *candida stellatoidea*.

In view of the antifungal activities of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient). The compounds of this invention are those of the formula:

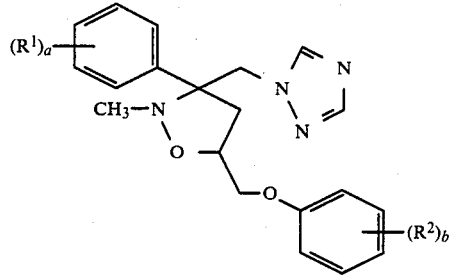

and pharmaceutically acceptable acid addition salts thereof in the form of their enantiomers, or mixtures of their enantiomers including diastereoisomeric pairs of such enantiomers,
wherein;
a=1 or 2,
b=1 or 2,
$R^1$ is selected from hydrogen, lower alkyl, halogen (preferably chlorine), lower alkoxy, and combinations thereof, provided that the ortho position is hydrogen and $R^2$ is selected from hydrogen, lower alkyl, halogen (preferably chlorine and fluorine), lower alkoxy, alkoxycarbonyl, alkanoylamino, nitro, and combinations thereof. By halogen is meant chlorine, bromine, fluorine and iodine. By lower alkyl and lower alkoxy is meant $C_1$-$C_4$ which may be a branched or unbranched chain. Compounds having ortho substitution of the upper phenyl group were not prepared probably due to steric hindrance.

The title 3-(substituted phenyl)-3-(1H-1,2,4-triazol-1-yl)methyl-2-methyl-5-[substituted phenoxy)methyl]-isoxazolidine derivatives are obtained as mixtures of cis-and trans- diastereomers due to the presence in the isoxazolidine ring of two asymmetric carbon atoms. The diastereomeric mixture is conveniently separated by flash-chromatography on silica gel using halogenated hydrocarbons (preferably methylene chloride and chloroform), alkanols (preferably methanol and ethanol), and ethyl acetate as eluents. The eluents may be used alone or in combinations such as the ones comprised of 95-99% halogenated hydrocarbon and 1-5% alkanol by volume. The stereochemistry of the two asymmetric carbon atoms in the isoxazolidine ring may be determined by conventional methods that include X-ray crystallography, nuclear magnetic resonance spectroscopy, circular dichroism and optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)- dibenzoyltartaric acid and the like. The compounds can be prepared as illustrated in the following diagram. The synthesis of the nitrone precursors 1 is accomplished by reacting an appropriately substituted triazolylacetophenone compound with N-methylhydroxylamine hydrochloride as disclosed in our co-pending application, Ser. No. 900,856 filed concurrently herewith and commonly assigned entitled "α-Substituted Ketonitrone Derivatives" whose disclosure is incorporated herein by reference. Reaction of the N-methyl-1-phenyl-2-(1H-1,2,4-triazol-1-yl) ethanimine N-oxide derivative 1 with an allyl (substituted)- phenyl ether (2) provides a diastereomeric mixture of the desired cis- and trans-3-(substituted phenyl)-3-(1H-1,2,4-triazol-1-yl)methyl-2-methyl-5-[(substituted phenoxy)methyl]isoxazolidine derivative 3.

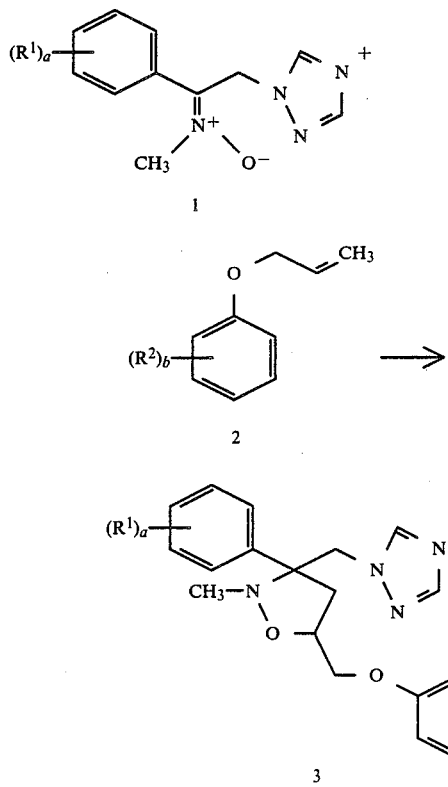

The compounds of the invention are all basic and thus can form salts with pharmaceutically acceptable inorganic and organic acids such as, for example, acetic acid, maleic acid, malic acid, fumaric acid, succininc acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

EXAMPLE 1

3-(3-Methylphenyl)-3-(1H-1,2,4-triazol-1-yl)methyl-2-methyl-5-[(2-nitrophenoxy)methyl]isoxazolidine (3, $R^1=3—CH_3$, $R^2=2—NO_2$)

A solution of 8.0 g (35 mmol) of N-methyl-1-(3-methylphenyl)-2-(1H-1,2,4-triazol-1-yl)ethanimine N-oxide (1, $R^1=3—CH_3$) [prepared by reacting 2-(1H-1,2,4-triazol-1-yl)-3'-methylacetophenone (7.04 g, 0.035 mol) with N-methylhydroxylamine hydrochloride (3.51 g, 0.042 mol) and sodium bicarbonate (3.53 g, 0.042 mol) in 100 ml of ethanol] and 9.34 g (52 mmol) of allyl 3-methylphenyl ether (2, $R^2=2—NO_2$) in 200 ml of toluene was refluxed under nitrogen atmosphere for 35 hours. Upon cooling to room temperature, the solvent was removed under reduced pressure leaving a dark oil which was dissolved in ethyl acetate. Addition of ether caused crystallization to occur, yielding 8.94 g (62%) of compound 3 ($R^1=3—CH_3$, $R^2=2—NO_2$). The resulting cis and trans-diastereomeric mixture of the title compound was flash-chromatographed on neutral silica gel using chloroform-methanol (99:1) by volume as eluent. Isomer A has a melting point of 149°–152° C. (ethyl acetate).

Anal. Calcd for $C_{21}H_{23}N_5O_4$: C, 61.60; H, 5.66; N, 17.10. Found: C, 61.27; H, 5.93; N, 16.94.

EXAMPLE 2

3-Phenyl-3-(1H-1,2,4-triazol-1-yl)methyl-2-methyl-5-(phenoxymethyl)isoxazolidine (3, $R^1=R^2=H$)

Compound 3 ($R^1=R^2=H$) was prepared by a procedure similar to that described in Example 1 by reacting N-methyl-1-phenyl-2-(1H-1,2,4-triazol-1-yl)ethanimine N-oxide (1, $R^1=H$) with allyl phenyl ether (2, $R^2=H$). The resulting cis- and trans-diastereomeric mixture of the title compound was flash-chromatographed on neutral silica gel using chloroform-methanol (99:1 by volume) as eluent. Isomer A has a melting point 68°–75° C. (ethyl acetate-hexane, 1:1 by volume).

Anal. Calcd for $C_{20}H_{22}N_4O_2$: C, 68.55; H, 6.33; N, 15.99. Found: C, 68.70; H, 6.44; N, 15.95.

EXAMPLE 3

3-Phenyl-3-(1H-1,2,4-triazol-1-yl)methyl-2-methyl-5-[(4-chlorophenoxy)methyl]isoxazolidine (3, $R^1=H$, $R^2=4—Cl$)

Compound 3 ($R^1=H$, $R^2=4—Cl$) was prepared by a procedure similar to that described in Example 1 by reacting N-methyl-1-phenyl-2-(1H-1,2,4-triazol-1-yl)ethanimine N-oxide (1, $R^1=H$) with allyl 4-chlorophenyl ether (2, $R^2=4—Cl$). The resulting cis- and trans-diastereomeric mixture of compound 3 ($R^1=H$, $R^2=4—Cl$) was flash-chromatographed on neutral silica gel using chloroform-methanol (98:2 by volume) as eluent. Isomer A has a melting point of 144°–147° C. (ethyl acetate).

Anal. Calcd for $C_{20}N_{21}ClN_4O_2$: C, 62.42; H, 5.50; N, 14.56; Cl, 9.21. Found: C, 62.40; H, 5.54; N, 14.54; Cl, 9.14.

EXAMPLE 4

3-Phenyl-3-(1H-1,2,4-triazol-1-yl)methyl-2-methyl-5-[(4-fluorophenoxy)methyl]isoxazolidine (3, $R^1=H$, $R^2=4—F$)

Compound 3 ($R^1=H$, $R^2=4—F$) was prepared by a procedure similar to that described in Example 1 by reacting N-methyl-1-phenyl-2-(1H-1,2,4-triazol-1-yl)ethanimine N-oxide (1, $R^1=H$) with allyl 4-fluorophenyl ether (2, $R^2=4—F$). The resulting cis- and trans-diastereomeric mixture of derivative 3 ($R^1=H$, $R^2=4—F$) was flash-chromatographed on neutral silica gel using chloroform-methanol (98:2 by volume) as eluent. Isomer A has a melting point of 115°–120° C. (ethyl acetate).

Anal. Calcd for $C_{20}H_{21}FN_4O_2$: C, 65.20; H, 5.75; N, 15.21; F, 5.16. Found: C, 65.13; H, 5.79; N, 15.13; F, 5.26.

EXAMPLE 5

3-Phenyl-3-(1H-1,2,4-triazol-1-yl)methyl-2-methyl-5-[(4-acetamidophenoxy) methyl]isoxazolidine (3, $R^1=H$, $R^2=4—NHCOCH_3$)

Compound 3 ($R^1=H$, $R^2=4—NHCOCH_3$) was prepared by a procedure similar to that described in Example 1 by reacting N-methyl-1-phenyl-2-(1H-1,2,4-triazol-1-yl)ethanimine N-oxide (1, $R^1=H$) with 4-acetamidophenyl allyl ether (2, $R^2=4—NHCOCH_3$). The resulting cis- and trans-diastereomeric mixture of compound 3 ($R^1$=H, $R^2$=4—NHCOCH$_3$) was flash-chromatographed on neutral silica gel using chloroform-methanol (97:3 by volume) as eluent. Isomer A has a melting point of 186°–189° C. (benzene-methanol, 1:1 by volume).

Anal. Calcd for $C_{22}H_{25}N_5O_3$: C, 64.85; H, 6.18; N, 17.19. Found: C, 64.80; H, 6.26; N, 17.35.

EXAMPLE 6

3-(4-Chlorophenyl)-3-(1H-1,2,4-triazol-1-yl)methyl-2-methyl-5-(phenoxymethyl)isoxazolidine (3, $R^1$=4—Cl, $R^2$=H)

Compound 3 ($R^1$=4—Cl, $R^2$=H) was prepared by a procedure similar to that described in Example 1 by reacting 1-(4-chlorophenyl)-N-methyl-2-(1H-1,2,4-triazol-1-yl)-ethanimine N-oxide (1, $R^1$=4—Cl) with allyl phenyl ether (2, $R^2$=H).

The resulting cis- and trans-diastereomeric mixture of compound 3 ($R^1$=4—Cl, $R^2$=H) was flash-chromatographed on neutral silica gel using chloroform-methanol (98:2 by volume) as eluent. Isomer A has a melting point of 135°–139° C. (ethyl acetate-hexane, 1:1 by volume).

Anal. Calcd for $C_{20}H_{21}ClN_4O_2$: C, 62.42; H, 5.50; N, 14.56; Cl, 9.21. Found: C, 62.37; H, 5.64; N, 14.47; Cl, 9.54. Isomer B has a melting point of 97°–100° C. (ethyl acetate-hexane, 1:1 by volume).

Anal. Calcd for $C_{20}N_{21}ClN_4O_2$: C, 62.42; H, 5.50; N, 14.56; Cl, 9.21. Found: C, 61.68; H, 5.51; N, 14.40; Cl, 10.21.

EXAMPLE 7

3-(4-Chlorophenyl)-3-(1H-1,2,4-triazol-1-yl)methyl-2-methyl-5-[(4-chlorophenoxy) methyl]isoxazolidine (3, $R^1$=$R^2$=4—Cl)

Compound 3 ($R^1$=$R^2$=4—Cl) was prepared by a procedure similar to that described in Example 1 by reacting 1-(4-chlorophenyl)-N-methyl-2-(1H-1,2,4-triazol-1-yl)ethanimine N-oxide (1, $R^1$=4—Cl) with allyl 4-chlorophenyl ether (2, $R^2$=4—Cl). The resulting cis- and trans-diastereomeric mixture of the title compound was purified by high-pressure liquid chromatography on neutral silica gel using chloroform-methanol (98:2 by volume) as eluent. Isomer A has a melting point of 125°–129° C. (ethyl acetate).

Anal. Calcd for $C_{20}H_{20}Cl_2N_4O_2$: C, 57.29; H, 4.81; N, 13.36; Cl, 16.91. Found: C, 57.30; H, 4.89; N, 13.37; Cl, 16.74. The above preparation was repeated except that nitrone 1 was prepared using sodium acetate in place of sodium bicarbonate.

EXAMPLE 8

3-(4-Chlorophenyl)-3-(1H-1,2,4-triazol-1-yl)methyl-2-methyl-5-[(4-methoxyphenoxy)methyl]isoxazolidine (3, $R^1$=4—Cl, $R^2$=4—OCH$_3$)

Compound 3 ($R_1$=4—Cl, $R^2$=4—OCH$_3$) was prepared by a procedure similar to that described in Example 1 by reacting 1-(4-chlorophenyl)-N-methyl-2-(1H-1,2,4-triazol-1-yl)-ethanimine N-oxide (1, $R^1$=4—Cl) with allyl 4-methoxyphenyl ether (2, $R^2$=4—OCH$_3$). The resulting cis- and trans-diastereomeric mixture of compound 3 ($R^1$=4—Cl, $R^2$=4—OCH$_3$) was flash-chromatographed on neutral silica gel using chloroform-methanol (98:2 by volume) as eluent. Isomer A has a melting point of 109°–111° C. (ethyl acetate-hexane, 1:1 by volume).

Anal. Calcd for $C_{21}H_{23}ClN_4O_3$: C, 60.79; H, 5.59; N, 13.50; Cl, 8.55. Found: C, 60.75; H, 5.69; N, 13.48; Cl, 8.59.

EXAMPLE 9

3-(4-Chlorophenyl)-3-(1H-1,2,4-triazol-1-yl)methyl-2-methyl-5-[(4-chloro-3-methyl phenoxy)methyl]isoxazolidine (3, $R_1$=4—Cl, $R^2$=4—Cl, 3—CH$_3$)

Compound 3 ($R_1$=4—Cl, $R^2$=4—Cl, 3—CH$_3$) was prepared by a procedure similar to that described in Example 1 by reacting 1-(4-chlorophenyl)-N-methyl-2-(1H-1,2,4-triazol-1-yl)ethanimine N-oxide (1, $R^1$=4—Cl) with allyl 4-chloro-3-methylphenyl ether (2, $R^2$=4—Cl, 3—CH$_3$). The resulting cis- and trans-diastereomeric mixture of the title compound was flash-chromatographed on neutral silica gel using chloroform-methanol (98:2 by volume) as eluent. Isomer A has a melting point of 135°–139° C. (ethyl-hexane, 1:1 by volume)

Anal. Calcd $C_{21}H_{22}Cl_2N_4O_2$: C, 58.21; H, 5.12; N, 12.93; Cl, 16.36. Found: C, 58.41; H, 5.29; N, 12.89; Cl, 21.71.

EXAMPLE 10

3-(4-Chlorophenyl)-3-(1H-1,2,4-triazol-1-yl)methyl-2-methyl-5-[(4-acetamidophenoxy)methyl]isoxazolidine (3, $R^1$=4—Cl, $R^2$=4—NHCOCH$_3$)

Compound 3 ($R^1$=4—Cl, $R^2$=4—NHCOCH$_3$) was prepared by a procedure similar to that described in Example 1 by reacting 1-(4-chlorophenyl)-N-methyl-2-(1H-1,2,4-triazol-1-yl)-ethanimine N-oxide (1, $R^1$=4—Cl) with 4-acetamidophenyl allyl ether (2, $R^2$=4—NHCOCH$_3$). The resulting cis- and trans-diastereomeric mixture of compound 3 ($R^1$=4—Cl, $R^2$=4—NHCOCH$_3$) was flash-chromatographed on neutral silica gel using chloroform-methanol (99:1 by volume) as eluent. Isomer A has a melting point of 150°–152° C. (benzene).

Anal. Calcd for $C_{22}H_{24}ClN_5O_3$: C, 59.79; H, 5.47; N, 15.85; Cl, 8.02. Found: C, 59.68; H, 5.72; N, 15.44; Cl, 7.73.

EXAMPLE 11

3-(4-Methoxyphenyl)-3-(1H-1,2,4-triazol-1-yl)methyl-2-methyl-5-[(4-chlorophenoxyl)methyl)]isoxazolidine (3, $R^1$=4—OCH$_3$, $R^2$=4—Cl)

Compound 3 ($R^1$=4—OCH$_3$), $R^2$=4—Cl) was prepared by a procedure similar to that described in Example 1 by reacting 1-(4-methoxyphenyl)-N-methyl-2-(1H-1,2,4-triazol-1-yl)-ethanimine N-oxide (1, $R^1$=4—OCH$_3$) with allyl 4-chlorophenyl ether (2, $R^2$=4—Cl). The resulting cis- and trans-diastereomeric mixture of the title derivative was flash-chromatographed on neutral silica gel using chloroform-methanol (98:2 by volume) as eluent. Isomer A has a melting point of 143°–146° C. (ethyl acetate).

Anal. Calcd for $C_{21}H_{23}ClN_4O_3$: C, 60.79; H, 5.59; N, 13.50; Cl, 8.55. Found: C, 60.92; H, 5.67; N, 13.56; Cl, 8.64.

EXAMPLE 12

3-(4-Chlorophenyl)-3-(1H-1,2,4-triazol-1-yl)methyl-2-methyl-5-{[4-(methoxycarbonyl)phenoxyl]methyl}isoxazolidine (3, $R^1$=4—Cl, $R^2$=4—CO$_2$CH$_3$)

Compound 3 ($R^1$=4—Cl, $R^2$=4—CO$_2$CH$_3$) was prepared by a procedure similar to that described in Example 1 by reacting 1-(4-chlorophenyl)-N-methyl-2-(1H-1,2,4-triazol-1yl)-ethanimine N-oxide (1, $R^1=4$—Cl) with methyl 4-allyloxybenzoate (2, $R^2=4$—$CO_2CH_3$). The resulting cis- and transdiastereomeric mixture of the title derivative was flash-chromatographed on neutral silica gel using chloroform-methanol (98:2 by volume) as eluent. Isomer A has a melting point of 153°–156° C. (ethyl acetate).

Anal. Calcd for $C_{22}H_{23}ClN_4O_4$: C, 59.66; H, 5.23; N, 12.65; Cl, 8.00. Found: C, 59.64; H, 5.32; N, 12.58; Cl, 8.09.

Isomer B has a melting point of 145°–148° C. (ethyl acetate-hexane, 1:1 by volume).

Anal. Calcd for $C_{22}H_{23}ClN_4O_4$: C, 59.66; H, 5.23; N, 12.65; Cl, 8.00. Found: C, 59.59; H, 5.40; N, 12.53; Cl, 5.93.

We claim:

1. A compound of the formula:

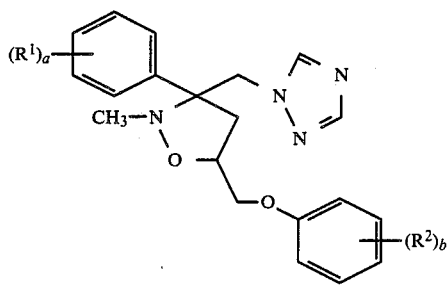

or a pharmaceutically acceptable acid addition salt thereof in the form of their enantiomers, or mixtures of their enantiomers including diastereoisomeric pairs of such enantiomers, wherein;

a=1 or 2, b=1 or 2, $R^1$ is selected from hydrogen, lower alkyl, halogen, lower alkoxy, and combinations thereof, provided that ortho position is hydrogen and $R^2$ is selected from hydrogen, lower alkyl, halogen, lower alkoxy, alkoxycarbonyl, alkanoylamino, nitro, and combinations thereof.

2. The compound of claim 1 wherein the compound is 3-(3-methylphenyl)-3-(1H-1,2,4-triazol-1-yl)methyl-2-methyl-5-[(2-nitrophenoxy)methyl]isoxazolidine.

3. The compound of claim 1 wherein the compound is 3-phenyl-3-(1H-1,2,4-triazol-1-yl)methyl-2-methyl-5-(phenoxymethyl)isoxazolidine.

4. The compound of claim 1 wherein the compound is 3-phenyl-3-(1H-1,2,4-triazol-1-yl)methyl-2-methyl-5-[(4-chlorophenoxy)methyl]isoxazolidine.

5. The compound of claim 1 wherein the compound is 3-phenyl-3-(1H-1,2,4-triazol-1-yl)methyl-2-methyl-5-[(4-fluorophenoxy)methyl]isoxazolidine.

6. The compound of claim 1 wherein the compound is 3-phenyl-3-(1H-1,2,4-triazol-1-yl)methyl-2-methyl-5-[(4-acetamidophenoxy]methyl)isoxazolidine.

7. The compound of claim 1 wherein the compound is 3-(4-chlorophenyl)-3-(1H-1,2,4-triazol-1-yl)methyl-2-methyl-5-(phenoxymethyl)isoxazolidine.

8. The compound of claim 1 wherein the compound is 3-(4-chlorophenyl)-3-(1H-1,2,4-triazol-1-yl)methyl-2-methyl-5-[(4-chlorophenoxy)methyl]isoxazolidine.

9. The compound of claim 1 wherein the compound is 3-(4-chlorophenyl)-3-(1H-1,2,4-triazol-1-yl)methyl-2-methyl-5-[(4-methoxyphenoxy)methyl]isoxazolidine.

10. The compound of claim 1 wherein the compound is 3-(4-chlorophenyl)-3-(1H-1,2,4-triazol1-yl)methyl-2-methyl-5-[(4-chloro-3-methylphenoxy)methyl]-isoxazolidine.

11. The compound of claim 1 wherein the compound is 3-(4-chlorophenyl)-3-(1H-1,2,4-triazol1-yl)methyl-2-methyl-5-[(4-acetamidophenoxy)methyl]isoxazolidine.

12. The compound of claim 1 wherein the compound is 3-(4-methoxyphenyl)-3-(1H-1,2,4-triazol1-yl)-methyl-2-methyl-5-[(4-chlorophenoxy)methyl]-isoxazolidine.

13. The compound of claim 1 wherein the compound is 3-(4-chlorophenyl)-3-(1H-1,2,4-triazol1-yl)methyl-2-methyl-5-{[4-methoxycarbonyl)phenoxyl]-methyl}isoxazolidine.

14. The compound of claim 1 wherein the compound is a diastereoisomeric pair of enantiomers.

* * * * *